United States Patent
Ruijter et al.

(10) Patent No.: US 8,686,145 B2
(45) Date of Patent: Apr. 1, 2014

(54) PROCESS FOR THE PREPARATION OF α-ACYLOXY β-FORMAMIDO AMIDES

(75) Inventors: Eelco Ruijter, Woerden (NL); Romano Orru, Haarlem (NL); Anass Znabet, Amsterdam (NL); Marloes Polak, Voorhout (NL); Nicholas Turner, Manchester (GB)

(73) Assignee: Vereniging Voor Christelijk Hoger Onderwijs, Wetenschappelijk Onderzoek en Patientenzorg C/O Technology Transfer Officer VU & Vumc, Amsterdam (NL)

( * ) Notice: Subject to any disclaimer, the term of this patent is extended or adjusted under 35 U.S.C. 154(b) by 0 days.

(21) Appl. No.: 13/581,173

(22) PCT Filed: Sep. 16, 2010

(86) PCT No.: PCT/EP2010/063657
§ 371 (c)(1),
(2), (4) Date: Sep. 13, 2012

(87) PCT Pub. No.: WO2011/103933
PCT Pub. Date: Sep. 1, 2011

(65) Prior Publication Data
US 2012/0330015 A1 Dec. 27, 2012

Related U.S. Application Data

(60) Provisional application No. 61/307,873, filed on Feb. 25, 2010.

(51) Int. Cl.
| | |
|---|---|
| C07C 291/10 | (2006.01) |
| C07D 209/52 | (2006.01) |
| C07D 209/58 | (2006.01) |
| C07D 209/94 | (2006.01) |
| C07D 241/24 | (2006.01) |
| C07D 403/06 | (2006.01) |

(52) U.S. Cl.
USPC ............ 544/406; 558/302; 560/238; 560/251

(58) Field of Classification Search
None
See application file for complete search history.

(56) References Cited

FOREIGN PATENT DOCUMENTS

WO WO 2007/022450 2/2007 ............ B01D 21/26

OTHER PUBLICATIONS

Ping Xu, et al. (2002) "Synthesis of a peptidomimetic HCMV protease inhibitor library." *Synthesis*, *(Stuttgart) Y.*, 8:1017-1026.
Velasquez, et al. (2007) "Application of ring-closing metathesis for the synthesis of macrocyclic peptidomimetics as inhibitors of HCV NS3 protease." *Organic Letters*, 9(16):3061-3064.
Yip, et al. (2004) "P4 and P1' optimization of bicycloproline P2 bearing tetrapeptidyl alphaketoamides as HCV protease inhibitors.", *Bioorg. Med. Chem. Lett.*, 14(19):5007-5011.
International Search Report (ISR) and Written Opinion in PCT/EP2010/063657 dated Jan. 24, 2011.

*Primary Examiner* — Kamal Saeed
(74) *Attorney, Agent, or Firm* — Harness, Dickey & Pierce, P.L.C.

(57) ABSTRACT

The present invention relates to a process for the preparation of a compound of the general Formula (I), comprising: a) reacting a compound of the general Formula (II) with a compound of the Formula III $R^2COOH$ and a compound of the general Formula IV $R^3NC$ under such conditions that compound I is formed, wherein $R^1$ represents a substituted or unsubstituted alkyl, alkenyl, alkynyl, aromatic or non-aromatic, mono-, di- or tricyclic, or heterocyclic structure, and $R^2$ represents a substituted or unsubstituted alkyl, alkenyl, alkynyl, aromatic or non-aromatic, mono-, di- or tricyclic, or heterocyclic structure, and $R^3$ represents a substituted or unsubstituted alkyl, alkenyl, or alkynyl structure. In further aspect the subject invention relates to the use of the obtained products as intermediates for various peptidomimetics, and preferably as a building block in a convergent synthesis of prolyl dipeptide structures.

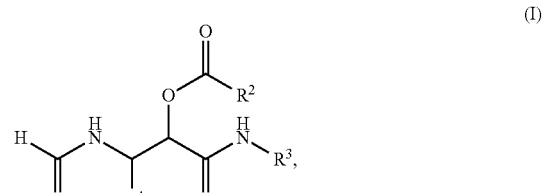

(I)

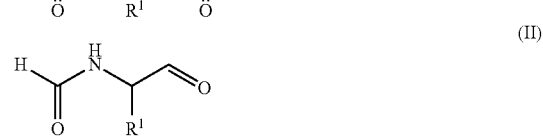

(II)

15 Claims, No Drawings

PROCESS FOR THE PREPARATION OF α-ACYLOXY β-FORMAMIDO AMIDES

CROSS-REFERENCE TO RELATED APPLICATIONS

This application is a national phase application of PCT Application No. PCT/EP2010/063657, filed on Sep. 16, 2010, which claims the benefit and priority to U.S. Patent Application No. 61/307,873, filed Feb. 25, 2010. The entire disclosures of the applications identified in this paragraph are incorporated herein by references.

FIELD OF THE INVENTION

The present invention relates to α-acyloxy β-formamido amides, methods for their preparation, and their use as intermediate for the preparation of isocyanide building block for the preparation of prolyl peptide inhibitors of disease-associated targets.

BACKGROUND OF THE INVENTION

α-hydroxy-β-aminocarboxylic acid and amide derivatives are found in a variety of natural products and pharmaceutically active substances.

Subunits incorporating the α-hydroxy-β-aminocarboxylic acid motif have been termed "norstatine" derivatives, and serve as key intermediates for the synthesis of the general class of P1-α-ketocarboxylic transition-state inhibitors of serine or cysteine proteases. Such inhibitors are finding increasing applications in medicine for the treatment of a diverse array of disease states including thrombosis, cancer, and osteoporosis.

Towards this end, α-hydroxy-β-aminocarboxylic acid, ester and amide derivatives serve an important role as the most common precursors for the preparation of these α-hydroxy-β-aminocarboxylic acid-incorporating drug candidates.

Electrophilic α-dicarbonyl compounds are regarded as interesting and highly reactive functional arrays which are capable of undergoing a myriad of transformations.

Such chemical properties can be exploited in novel and therapeutically useful ways by strategically incorporating these reactive α-ketocarboxylic moieties into a peptidic or peptidomimetic matrix.

Multicomponent reactions (MCRs) such as the Passerini and Ugi reactions offer the ability to rapidly and efficiently generate collections of structurally and functionally diverse organic compounds. The Passerini reaction is a chemical reaction involving isocyanides, aldehydes or ketones, and carboxylic acids to form α-acyloxy amides. Compounds that are available through the Passerini reaction may form highly valuable building blocks in the convergent synthesis of compounds with medicinal effects, such as for instance the prolyl dipeptide inhibitors Telaprevir or Boceprevir.

WO2007/0022450 discloses for instance the preparation of a cyclopropylamide by the coupling of Cb-norvalinal with cyclopropyl isocyanide in the presence of trifluoroacetic acid. The obtained compound is then deprotected, and the aminoalcohol then employed in a synthesis of Telaprevir. However, the disclosed synthesis is cumbersome, and only allows for a limited yield and variation of the building blocks involved.

Accordingly, the access to such compound through a more selective and higher yielding route would be highly desirable.

SUMMARY OF THE INVENTION

The subject invention now provides for a synthesis of α-hydroxy-aminocarboxylic acid derivatives such as to α-acyloxy β-formamido amides that advantageously can be employed in multicomponent reactions (MCRs), such as Passerini and Ugi reactions, which allow convergent syntheses with high atom and step efficiency in good yield.

Accordingly, the present invention relates to a process for the preparation of a compound of the general formula I

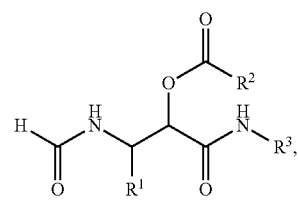

(I)

comprising:
a) reacting a compound of the general formula II:

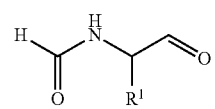

(II)

with a compound of the formula III:

$R^2$—COOH     (III), and a compound of the general formula IV

$R^3$—NC     (IV)

wherein $R^1$ represents a hydrogen atom, a substituted or unsubstituted alkyl, alkenyl, alkynyl, aromatic or non-aromatic, monocyclic, polycyclic or alkylcycloalkyl or a heterocyclic structure;
$R^2$ represents a substituted or unsubstituted alkyl, alkenyl, alkynyl, aromatic or non-aromatic, mono-, di- or tricyclic, or heterocyclic structure; and
$R^3$ represents a substituted or unsubstituted alkyl, alkenyl, or alkynyl structure, or a protective group that can reversible be removed.

In a first aspect, the present invention provides novel methods for the synthesis of α-hydroxy-β-amino acid and amide derivatives according to formula I and intermediates thereto. These derivatives may be advantageously be employed as intermediates for synthesis of peptidyl α-ketoamides and α-hydroxy-β-amino carboxylic acid derivatives which are useful as inhibitors of certain proteases, including serine and cysteine proteases.

The process preferably involves reacting an N-terminally protected amino aldehyde with an isonitrile and a carboxylic acid to give an amino α-acyloxy carboxamide. The acyl group may then be removed to give the derivative, or may advantageously remain in position. Alternatively, the protecting group may removed and an acyl shift may advantageously take place. The reaction is performed under such conditions that compound I is formed.

The process according to present invention provides an improved synthetic route to intermediates for the end target compounds, with economy of synthesis, namely fewer synthetic steps, improved yields, less consumption of reagents and fewer side products than are obtained following conventional synthetic routes.

In the process according to the invention, $R^1$ preferably represents a hydrogen, a straight chain alkyl, a branched chain alkyl, a cycloalkyl, an alkylene-cycloalkyl preferably —CH$_2$-cyclopropyl or —CH$_2$-cyclobutyl, an aryl, alkylene-aryl, SO$_2$-alkyl, SO$_2$-aryl, alkylene-SO$_2$-aryl, -alkylene-SO$_2$-alkyl, heterocyclyl or alkylene-heterocyclyl; CH$_2$CO—X—H, —CH$_2$CO—X-straight chain alkyl, —CH$_2$CO—X-branched chain alkyl, —CH$_2$CO—X-cycloalkyl, —CH$_2$CO—X-alkylene-cycloalkyl, —CH$_2$CO—X-aryl, —CH$_2$CO—X-alkylene-aryl, —CH$_2$CO—X-heterocyclyl, —CH$_2$CO—X-alkylene-heterocyclyl or —CH$_2$CO-aryl; wherein X represents O, S or NH.

$R^2$ preferably represents hydrogen, a straight chain alkyl, a branched chain alkyl, a cycloalkyl, an alkylene-cycloalkyl, an aryl, and/or alkylene-aryl.

$R^3$ preferably represents a straight chain alkyl, a branched chain alkyl, a cycloalkyl, an alkylene-cycloalkyl, an aryl, and/or alkylene-aryl.

In a preferred embodiment of the subject invention, $R^1$ represents an alkyl group such as ethyl or preferably n-propyl, or an alkylcycloalkyl group, such as cyclobutylmethyl. More preferably $R^2$ preferably is a lower carboxylic acid group, preferably an acetate group, and $R^3$ preferably is a cyclopropyl group.

The process according to the present invention further advantageously comprises a step b) of isolating the obtained compound I from the reaction mixture.

This may be done by any suitable method known to a skilled person, such as extraction, chromatographic separation, distillation, crystallization or otherwise suitable process or combinations thereof.

Alternatively, the compound remains in the reaction mixture, and the isocyanide compound is added to the mixture.

Preferably, the aldehyde compound according to formula II is derived from a substituted 2-amino-1-ethanol according to general formula V:

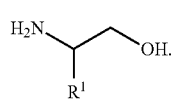

(V)

Preferably, the alcohol is enantiomerically substantially pure, since this allows accessing a large number of different stereoisomeric compounds from substituted alcohols, thus from relatively simple building blocks.

Compound II may advantageously be prepared from an substituted 2-amino-1-ethanol according to general formula V by A) N-formylation, and B) by a selective oxidation of the primary alcohol of the obtained N-formylated amino alcohol intermediate to an aldehyde.

Steps (A) and (B) may be performed by any suitable method known to a person skilled in the art.

Preferably, step (B) includes a Dess-Martin oxidation of the alcohol to an aldehyde.

The oxidation is advantageously performed by employing a Dess-Martin oxidation. In this way, the stereogenic centre and various substituents $R^1$ can be introduced from often commercially or synthetically readily available 2-aminoethanols. A so-called Dess-Martin oxidation employs the Dess-Martin Periodinane (DMP), a hypervalent iodine compound for the selective and very mild oxidation of alcohols to aldehydes or ketones, as disclosed for instance in Y. Yip, F. Victor, J. Lamar, R. Johnson, Q. M. Wang, J. I. Glass, N. Yumibe, M. Wakulchik, J. Munroe, S.-H Chen, *Bioorg. Med. Chem. Lett.* 2004, 14, 5007-5011.

The oxidation preferably may be performed in dichloromethane, chloroform of THF at room temperature, and is usually complete within 0.5-2 hours. Products are easily separated from the iodine-containing by-products after basic work-up.

Preferably, the Dess-Martin oxidation according to the invention is performed in the presence of compound IV, in such a way that the aldehyde II that is formed during the Dess-Martin oxidation immediately reacts in a Passerini reaction with the acetic acid that is formed as a by-product of the Dess-Martin oxidation as carboxylic acid III and isocyanide IV. This has the tremendous benefit that the atomic efficiency of the reaction is increased, since the Dess-Martin Periodinane (DMP) also provides a reactant for the second stage of the reaction, i.e., the Passerini three-component reaction. In addition, the combination of two reaction steps in one pot is advantageous in terms of both time and resources, since among other benefits less solvent and manpower are required due to the single workup stage, and since less separation steps by chromatography are required. Accordingly, compound II is advantageously not isolated after step B), but the isocyanide component IV is added to the reaction mixture after the oxidation is complete. In this case, the lower carboxylic acid, preferably acetic acid released from the Dess-Martin Periodinane acts as component III, thereby resulting in a carbon efficient process with minimal handling and isolation issues. Moreover, the aldehyde compounds obtained can directly be converted with high selectivity to compound (I) as defined herein above, which is usually more stable than the aldehyde component, thereby increasing the overall yield. Accordingly the present invention also relates to a process including combining the Dess-Martin oxidation in one pot with the Passerini reaction to afford α-acyloxy-β-formamido amides (I) directly.

The process according to the present invention further advantageously comprises a step c) of subjecting compound I to dehydrating conditions to obtain an isocyanide compound according to general formula VI:

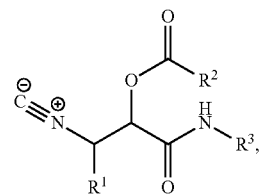

(VI)

wherein $R^1$, $R^2$ and $R^3$ are as defined herein above.

This may advantageously be achieved for instance by treatment of the formamido compound (I) with phosgene, diphosgene (trichloromethylchlorofolurate), triphosgene [bis(trichloromethyl) carbonate], and/or POCl$_3$. The reaction step (c) usually performed in the presence of a base, typically a tertiary amine base such as triethylamine or N-methylmorpholine.

Preferably, therefore, $R^2$ is a lower carboxylic acid, more preferably acetate.

In a preferred embodiment of the subject process, $R^1$ is preferably is an alkyl group, such as n-propyl, or an alkylcycloalkyl group, preferably —CH$_2$-cyclopropyl or —CH$_2$-cyclobutyl.

In a further preferred embodiment of the subject process, $R^3$ is a cycloalkyl or hydrogen, or a protective group as usually employed to reversibly protect primary amines.

In yet a further preferred embodiment of the subject process, $R^1$, $R^2$ and $R^3$ are chosen such that the compound according to formula VI has a structure according to general formula VII:

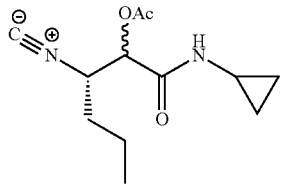
(VII)

In yet a further preferred embodiment of the subject process, $R^1$, $R^2$ and $R^3$ are chosen such that the compound according to formula VI has a structure according to general formula VIII:

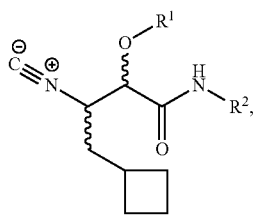
(VIII)

wherein $R^1$ represents a lower carboxylic acid group, preferably acetate, and $R^2$ represents reversibly attached protective group.

The isocyanide compound VI can advantageously be employed in reaction processes such as Ugi or related multicomponent reactions that make use of isocyanide compounds in the convergent synthesis of complex structures, such a prolyl dipeptide structures.

Accordingly, the subject process further advantageously comprises reacting the compound according to formula IV with a compound having the general formula IX:

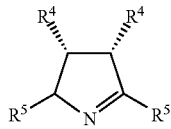
(IX)

or the respective diastereomers, and
a compound of the general formula X:

$R^7$—COOH         (X), to obtain a compound according to general formula XI or its respective diastereomers

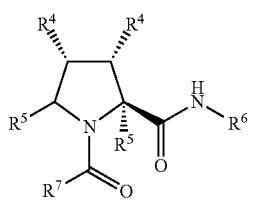
(XI)

wherein $R^4$ represents each independently, or jointly a substituted or unsubstituted alkyl, alkenyl, alkynyl, aromatic or non-aromatic, mono-, di- or tricyclic, or heterocyclic structure, and
$R^5$ represents each independently a hydrogen atom, a substituted or unsubstituted alkyl, alkenyl, alkynyl, aromatic or non-aromatic, mono-, di- or tricyclic, or heterocyclic structure, $R^6$ represents the structure derived from compound I wherein $R^1$, $R^2$ and $R^3$ are defined herein above, and
$R^7$ represents a substituted or unsubstituted alkyl, alkenyl, or alkynyl, or an aromatic or non-aromatic aromatic or non-aromatic, mono-, di- or tricyclic, or heterocyclic structure, and $R^7$ represents a substituted or unsubstituted alkyl, alkenyl, or alkynyl, or an aromatic or non-aromatic aromatic or non-aromatic, mono-, di- or tricyclic, or heterocyclic structure, under conditions that compound XI is formed.

In the case of $R^5$ being different from hydrogen, the diastereomers of compound IX referred to above include the following compounds of general formula IXa and IXb, respectively:

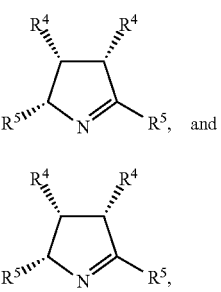
(IXa)

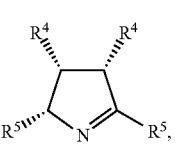
(XIb)

resulting predominantly in the compounds of general formula XIa and XIb, respectively:

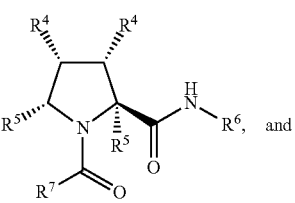
(XIa)

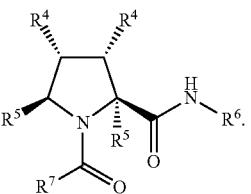
(XIb)

The (3R,7S)-diastereomers, i.e. the diastereomers having the opposite configuration of the substituents $R^4$ can also be employed, yielding the equivalent (3R,7S)-configured proline derivatives XI.

Preferably, both substituents $R^5$ represent hydrogen, and both substituents $R^4$ jointly form a substituted or unsubstituted 3-, 4-, 5-, 6-, 7- or 8 membered ring structure. More preferably, $R^4$ is chosen such that the compound according to formula I has the structure according to formula XII:

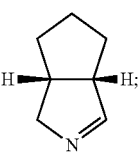
(XII)

according to formula XIII:

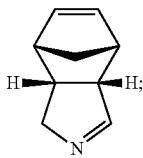

(XIII)

or according to formula XIV:

(XIV)

Preferably, R⁷ represents a structure according to general formula XV:

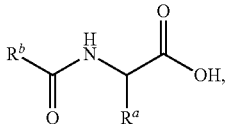

(XV)

wherein $R^a$ and $R^b$ each independently represents a hydrogen atom, a halogen atom, a lower alkyl group comprising from 1 to 4 carbon atoms, a lower alkyl group substituted by halogen, a cycloalkyl group, an aryl group, a lower alkoxy group, a lower thioalkyl group, a cycloalkyloxy group, an aralkyloxy group or an alkanoyl group; a hydroxyl group, a nitro group, a formyl group, an amino group which may be protected or substituted, a cycloalkyloxy, aralkyloxy, alkanoyl, ureido or mono-, di- or tricyclic heterocyclic group, all of which groups may optionally be substituted.

In a preferred embodiment of the subject process, the compound according to formula XII

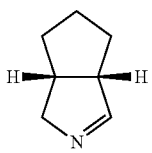

(XII)

is reacted with a compound according to general formula XVI:

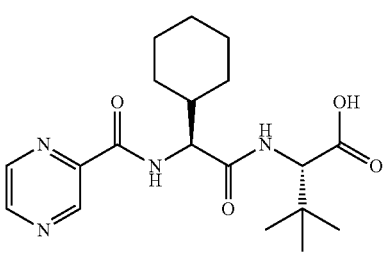

(XVI)

and a compound according to general formula VII as defined herein above to obtain a compound according to formula XVII:

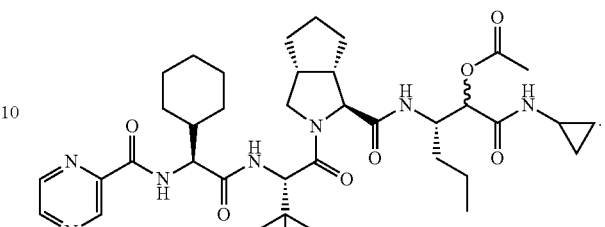

(XVII)

After the reaction, compound XVII may advantageously be isolated from the reaction mixture.

The subject process further preferably comprises subjecting the compound according to formula XVII to a saponification reaction to remove the acetate from the secondary alcohol at the α-hydroxy-β-amino acid structure.

The saponification preferably is carried out by contacting the compound according to formula XVII with an alkaline metal carbonate, preferably K₂CO₃, in a suitable solvent, to obtain a saponified alcohol product according to formula XVIIa (not depicted here). The subject invention also relates to compounds XVII and XVIIa.

The released intermediate compound XVIIa comprising the secondary alcohol is then subjected to a selective oxidation to a ketone to form compound XVIII,

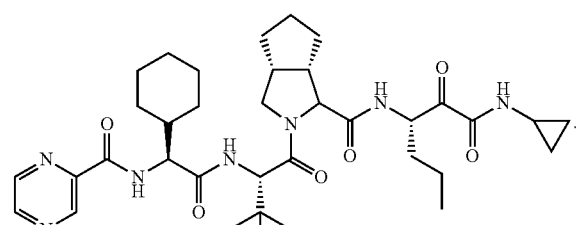

(XVIII)

This compound, which is also known as Telaprevir, could be prepared in higher yields than any previously disclosed processes according to the process of the present invention.

In a further preferred embodiment of the subject process, a compound according to general formula XVIII above is reacted with an acid compound according to general formula XIX:

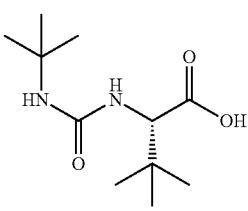

(XIX)

and an isocyanate compound according to the present invention according to general formula XXI:

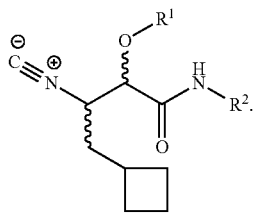
(XX)

This reaction will result in compound XXI,

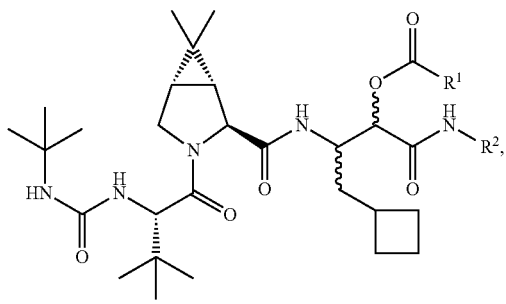
(XXI)

which may advantageously be saponified to a secondary alcohol and subsequently oxidized to a ketone, thereby yielding, after removal under suitable conditions of the R² group, a compound according to formula XXIII:

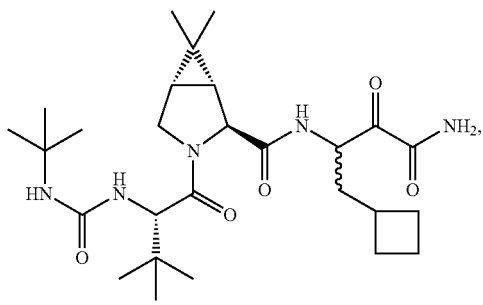
(XXII)

also known as Boceprevir.

The process according to the present invention advantageously permits to selectively produce the two diastereomers according to the general formula XXIIa:

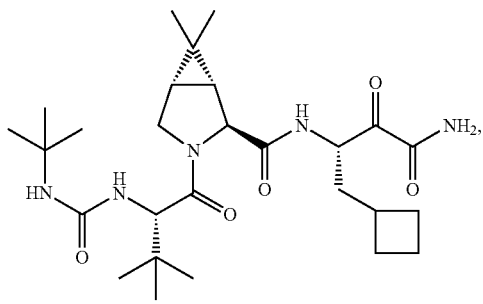
(XXIIa)

and according to the general formula XXIIb, respectively,

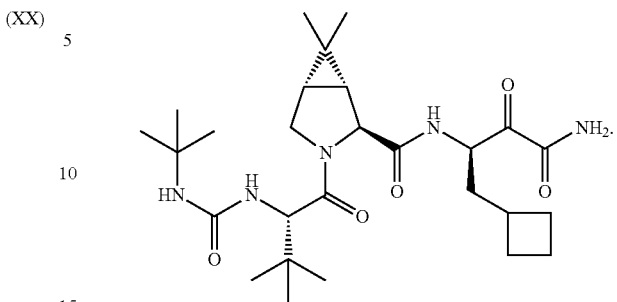
(XXIIb)

The subject invention therefore also relates to a process wherein XIIa or XIIb are selectively prepared, and to the thus obtained compounds XXIa or XXIb as well as to compounds XIIa or XIIb.

Suitable solvents for the subject reaction are polar protic and aprotic organic solvents, including methanol, ethanol, 2-propanol and other alcohol solvent, tetrahydrofuran, 1,4-dioxane, acetonitrile, and/or mixtures of these solvents with water or less polar organic solvents, such as dichloromethane or chloroform.

The saponification or removal of the ester group through hydrolysis may be performed by any suitable method known to a skilled person. Preferably, it is carried out by contacting the obtained reaction product according to formula I with an alkaline metal carbonate, more preferably $K_2CO_3$ in a suitable solvent, to obtain a saponified alcohol product. The saponified alcohol product may then advantageously be oxidised selectively at the secondary alcohol function, preferably without affecting the other structures on the compound, to yield a ketone compound.

The selective oxidation is preferably carried out by contacting the saponified alcohol product with a suitable oxidant in a suitable solvent. Suitable solvents include dichloromethane, THF, ethyl acetate, DMSO. Suitable oxidants include hypervalent iodine reagents such as IBX, Dess-Martin periodinane, etc., or a combination of TEMPO and PhI $(OAc)_2$ or related reagents.

The present invention further advantageously also relates to all novel intermediates obtainable by the subject process, more preferably to compounds XIV and XIX prior to saponification, to the compounds having the saponified secondary alcohols, and to all novel intermediates and building blocks.

EXPERIMENTAL PART

Example 1

Synthesis of (S)-2-Formamidopentanal (1)

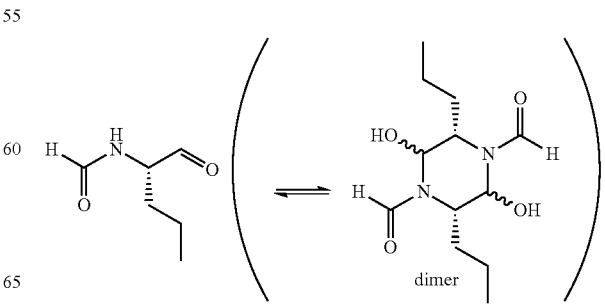

Compound (I) and its Dimeric Form

Dess-Martin periodinane (5.514 g, 13 mmol) was added to a solution of (S)-2-formamido-1-pentanol (1.31 g, 10 mmol) in $CH_2Cl_2$ (100 ml) at room temperature. The white suspension was stirred for 2 days and subsequently 35 ml MeOH was added and stirred for 30 minutes. The resulting suspension was filtrated and the filtrate was concentrated in vacuo. The crude product was purified by silica gel flash chromatography (cHex:EtOAc=1:4) to give compound I (1.08 g, 8.29 mmol, 83%) as a white solid. NMR analysis indicates that compound I is in equilibrium with its cyclic dimmer, which was found to form a mixture of diastereomers.

$[α]_D^{20}$=+37.6 (c=0.745, $CHCl_3$); $^1$H NMR assigned to the monomer (250.13 MHz, $CDCl_3$): δ=8.22 (s, 1H), 7.84 (s, 1H), 7.10 (m, 1H), 5.31 (m, 1H), 1.52 (m, 4H), 0.95 (m, 3H); $^{13}$C NMR assigned to the monomer (100.61 MHz, $CDCl_3$): 198.8 (CH), 161.7 (CH), 57.4 (CH), 30.8 ($CH_2$), 18.4 ($CH_2$), 13.7 ($CH_3$); $^1$H NMR assigned to the dimer (400.13 MHz, $CDCl_3$) 8.22 (s, 2H), 5.26 (m, 2H), 3.72 (m, 2H) 1.52 (m, 8H), 0.95 (m, 6H $^{13}$C NMR (100.61 MHz, $CDCl_3$) assigned to the dimer: 161.7 (CH), 89.8 (CH), 63.1 (CH), 30.8 (CH2), 18.4 (CH2), 13.7 (CH3); IR (neat): $ν_{max}$ ($cm^{-1}$): 3325 (s), 2959 (s), 1649 (s), 1530 (s), 1381 (m), 1123 (w); HRMS (ESI, 4500V): m/z calc. for $C_6H_{12}NO_2^+$ ($[M+H]^+$) 130.0863. found 130.0858.

Example 2

Synthesis from Compound I as Obtained in Example 1

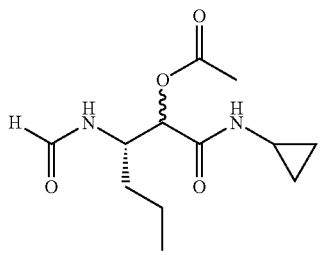 [SMILES: CCC[C@H](NC=O)C(OC(C)=O)C(=O)NC1CC1]

(3S)-2-acetoxy-N-cyclopropyl-3-formamidohexanoyl amide (3)

Aldehyde compound I (0.892 g, 6.91 mmol) was added to a solution of cyclopropyl isocyanide (0.410 g, 6.12 mmol) in $CH_2Cl_2$ (110 ml) and stirred for 5 minutes at room temperature. Acetic acid (0.711 ml, 0.747 g, 12.44 mmol) was added and the yellow reaction mixture was stirred for 3 days at room temperature. The reaction mixture was washed twice with 100 ml saturated $Na_2CO_3$, followed by drying with $Na_2SO_4$ and concentration in vacuo. The crude was purified by silica gel flash chromatography (5% MeOH in $CH_2Cl_2$, 1% triethylamine). (3S)-2-acetoxy-N-cyclopropyl-3-formamidohexanoyl amide (0.99 g, 3.87 mmol, 56%) was obtained as a white solid as a 78:22 mixture of diastereomers.

Example 3

In situ-preparation of (3S)-2-acetoxy-N-cyclopropyl-3-formamidohexanoyl amide (3) without isolation of the compound obtained in example 1

Dess-Martin periodinane (5.66 g, 12.3 mmol) was added to a solution of (S)—N-(1 hydroxypentan-2-yl)formamide (1.15 g, 8.8 mmol) in $CH_2Cl_2$ (12 ml) at room temperature. The white suspension was stirred for 60 minutes and subsequently cyclopropyl isocyanide (0.74 g, 10.0 mmol) was added and stirred for 48 hours. The resulting suspension was filtrated and washed twice with 10 ml saturated $Na_2CO_3$, followed by drying with $Na_2SO_4$ and concentration in vacuo. The crude product was purified by silica gel flash chromatography (5% MeOH in $CH_2Cl_2$, 1% triethylamine) to give compound 3 (1.34 g, 5.22 mmol, 60%) as a pale yellow solid as a 78:22 mixture of diastereomers.

$^1$H NMR (130° C., 400.13 MHz, DMSO-$d_6$): δ=8.03 (s, 1H), 7.52 (m, 1H), 7.30 (m, 1H), 4.89 (d, J=4.4, 1H), 4.28 (m, 1H), 2.65 (m, 1H), 2.17 (s, 3H), 1.27-1.47 (m, 4H), 0.89 (t, J=7.2, 3H), 0.63 (m, 2H), 0.48 (m, 2H); $^{13}$C NMR (125.78 MHz, DMSO-$d_6$): δ=169.8 (C), 168.5 (C), 160.6 (CH), 74.4 (CH), 47.5 (CH), 22.2 (CH), 18.4 ($CH_3$), 13.6 ($CH_3$), 5.7 ($CH_2$); IR (neat): $ν_{max}$ ($cm^{-1}$) 3283 (s), 2961 (w), 1744 (m), 1661 (s), 1530 (s), 1238 (s); HRMS (ESI, 4500V): m/z calcd. for $C_{12}H_{20}N_2O_4Na^+$ ($[M+Na]^+$) 279.1315. found 279.1325.

Example 4

Preparation of (3S)-2-acetoxy-N-cyclopropyl-3-isocyano-hexanoyl amide (4)

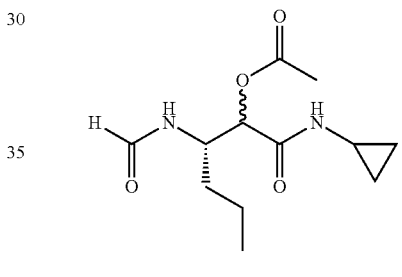

(3S)-2-acetoxy-N-cyclopropyl-3-isocyano-hexanoyl amide (4)

N-methylmorpholine (0.57 ml, 0.562 g, 5.56 mmol) was added to a solution of (S)-1-(cyclopropylamino)-3-formamido-1-oxohexan-2-yl acetate (0.713 g, 2.78 mmol) in $CH_2Cl_2$ (40 ml) at room temperature. The reaction mixture was cooled to −78° C. and triphosgene (0.289 g, 0.97 mmol) was quickly added and stirred for 5 minutes at this temperature. The resulting yellow solution was wanted up to −30° C. and was stirred for another 3 h. Subsequently, the reaction was quenched with water and extracted twice with $CH_2Cl_2$ (40 ml). The organic layers were collected, dried with $Na_2SO_4$ and concentrated in vacuo. The crude product was purified by silica gel flash chromatography (2% MeOH in $CH_2Cl_2$) to give 4 (0.578 g, 2.42 mmol, 87%) as a white solid.

$^1$H NMR (250.13 MHz, $CDCl_3$): δ=6.28 (s, 1H), 5.25 (d, J=2.5 Hz, 1H), 4.2 (m, 1H), 2.74 (m, 1H), 2.24 (s, 3H), 1.55 (m, 4H), 0.96 (m, 3H), 0.84 (m, 2H), 0.60 (m, 2H); $^{13}$C NMR (62.90 MHz, $CDCl_3$): δ=169.7 (C), 168.3 (C), 74.4 (CH), 47.5 (CH), 22.0 (CH), 20.6 ($CH_3$), 18.5 ($CH_2$), 13.5 ($CH_3$), 5.5 ($CH_2$); IR (neat): $ν_{max}$ ($cm^{-1}$): 3267 (s), 2959 (m), 1745 (m), 1643 (s), 1512 (m), 1221 (s); HRMS (ESI, 4500V): m/z calcd. for $C_{12}H_{18}N_2O_3Na^+$ ($[M+Na]^+$) 261.1210. found 261.1214.

Example 5

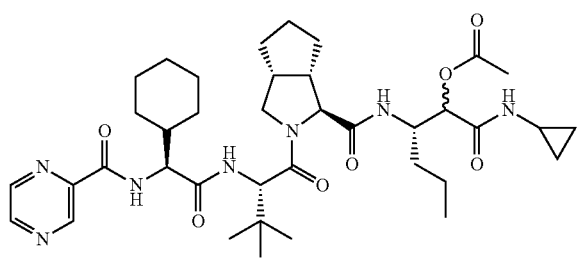 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(OC(C)=O)C(=O)NC1CC1]

General Structure of the Compound Obtained in Example 5

The Isocyanide obtained in Example 4 (0.549 g, 2.3 mmol) was dropwise added to a solution of (3S,&R) 3-azabicyclo-[3,3,0]oct-2-ene imine (0.252 g, 2.3 mmol) and (S)-2-((S)-2-cyclohexyl-2-(pyrazine-2-carboxamido)acetamido)-3,3-dimethylbutanoic acid (0.602 g, 1.60 mmol) in CH$_2$Cl$_2$ (5 ml) at room temperature. This yellow solution was stirred for 72 hours and afterwards diluted with 5 ml CH$_2$Cl$_2$. The reaction mixture was washed twice with saturated Na$_2$CO$_3$ solution (10 ml) and twice with saturated NH$_4$Cl. The organic layers were collected, dried with MgSO$_4$ and concentrated in vacuo. The crude product was purified by silica gel flash chromatography (5% MeOH in CH$_2$Cl$_2$) to give 5 (0.876 g, 1.21 mmol, 76%) as a mixture of diastereomers.

$^1$H NMR (500.23 MHz, CDCl$_3$): δ=9.50 (s, 1H), 8.75 (d, J=2.5, 1H), 8.59 (s, 1H), 8.35 (d, J=9.0, 1H), 6.84 (d, J=9.0, 1H), 6.44 (s, 1H), 5.20 (d, J=3.0, 1H), 4.74 (d, J=9.5, 1H), 4.58 (t, J=7.5, 1H), 4.38 (m, 1H), 3.37 (d, J=6.0, 1H), 2.82 (m, 1H), 2.69 (m, 1H), 2.11 (s, 3H), 1.26 (s, 2H), 0.97 (s, 9H), 0.86 (m, 3H), 0.84-2.00 (m, 21H), 0.76 (m, 2H), 0.51 (m, 2H); $^{13}$C NMR (125.78 MHz, CDCl$_3$): δ=170.5 (C), 169.3 (C), 162.9 (C), 147.4 (CH), 144.6 (CH), 144.2 (C), 142.8 (CH), 74.4 (CH), 66.6 (CH), 58.3 (CH), 56.6 (CH), 54.5 (CH$_2$), 44.9 (CH), 43.0 (CH), 41.3 (CH), 35.5 (C), 26.4 (CH$_3$), 20.8 (CH$_3$), 19.1 (CH$_2$), 13.8 (CH$_3$), 6.6 (CH$_2$); ν$_{max}$ (cm$^{-1}$): 3306 (m), 2928 (m), 2931 (m), 1743 (w), 1655 (m), 1520 (m), 1219 (m); HRMS (ESI, 4500 V): m/z calcd. for C$_{38}$H$_{57}$N$_7$O$_7$Na$^+$ ([M+Na]) 746.4212. found 746.4107.

Example 6

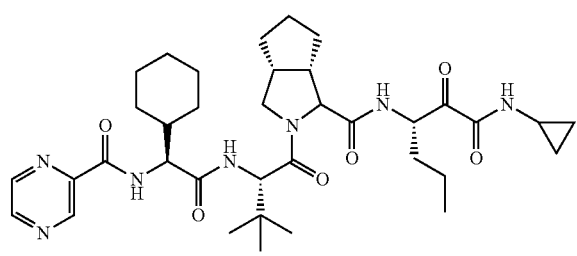 [SMILES: CCC[C@H](NC(=O)C1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

Telaprevir (Example 6)

250 μl of saturated K$_2$CO$_3$ was added to a solution of the compound obtained in Example 5 (0.514 g, 0.75 mmol) in MeOH (20 ml) at room temperature. The reaction mixture was stirred for 30 minutes at room temperature resulting in a pale yellow suspension. After full conversion (as judged by TLC analysis), the reaction mixture was washed with 20 ml brine, the aqueous layer was washed again with 10 ml CH$_2$Cl$_2$ (2×). The organic layers were collected, dried with MgSO$_4$ and concentrated in vacuo, to yield a pale yellow solid. The yellow solid was dissolved in CH$_2$Cl$_2$ (10 ml) and Dess-Martin periodinane (0.650 g, 1.532 mmol) was added at room temperature. The reaction mixture was stirred overnight before adding saturated NaHCO$_3$ solution (10 ml) and saturated Na$_2$S$_2$O$_3$ solution (10 ml). This mixture was stirred for 10 minutes, separated and the aqueous layers were washed with EtOAc (2×10 ml). The organic layers were collected, dried with MgSO$_4$ and concentrated in vacuo to give the crude product as an 83:13:4 mixture of diastereomers. After silica gel flash chromatography (1% MeOH in CH$_2$Cl$_2$), 5 (0.412 mg, 0.61 mmol, 80%) was obtained as a white solid. $^1$H NMR (500.23 MHz, DMSO-d$_6$): δ=9.19 (d, J=1.4 Hz, 1H), 8.91 (d, J=24.5 Hz, 1H), 8.76 (dd, J=1.5, 2.5 Hz, 1H), 8.71 (d, J=5.3 Hz, 1H), 8.49 (d, J=9.2 Hz, 1H), 8.25 (d, J=6.8 Hz, 1H), 8.21 (d, J=8.9 Hz, 1H), 4.94 (m, 1H), 4.68 (dd, J=6.5, 9.0 Hz, 1H), 4.53 (d, J=9.0 Hz, 1H), 4.27 (d, J=3.5 Hz, 1H), 3.74 (dd, J=8.0, 10 Hz, 1H), 2.74 (m, 1H), 3.64 (d, J=3.5 Hz, 1H), 0.92 (s, 9H), 0.87 (t, 3H), 0.84-1.40 (m, 23H), 0.65 (m, 2H), 0.56 (m, 2H); $^{13}$C NMR (125.78 MHz, CDCl$_3$): δ=197.0 (C), 171.8 (C), 170.4 (C), 169.0 (C), 162.1 (C), 161.9 (C), 147.9 (CH), 144.0 (C), 143.4 (CH), 56.4 (CH), 56.3 (CH), 54.2 (CH), 53.4 (CH), 42.3 (CH), 41.3 (CH), 32.1 (CH), 31.8 (CH), 31.6 (CH), 29.1 (CH), 28.0 (CH), 26.4 (CH$_3$); ν$_{max}$ (cm$^{-1}$): 3302 (m), 2928 (m), 2858 (w), 1658 (s), 1620 (s), 1561 (s), 1442 (m); HRMS (ESI, 4500 V): m/z calcd. for C$_{36}$H$_{53}$N$_7$O$_6$Na$^+$ ([M+Na]$^+$) 702.3950. found 702.3941.

The invention claimed is:

1. A process for preparing a compound of formula I:

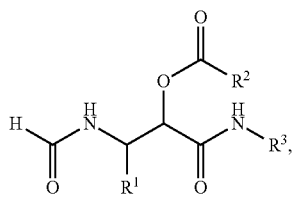

(I)

comprising:
a) reacting a compound of formula II:

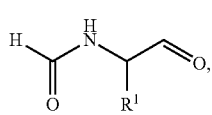

(II)

with a compound of formula III:

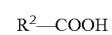

R$^2$—COOH  (III), and a compound of formula IV:

R$^3$—NC  (IV), under such conditions that a compound of formula I is formed,
wherein R$^1$ represents a substituted or unsubstituted alkyl, alkenyl, alkynyl, aromatic or non-aromatic, mono-, di- or tricyclic, or heterocyclic group, $R^2$ represents a substituted or unsubstituted alkyl, alkenyl, alkynyl, aromatic or non-aromatic, mono-, di- or tricyclic, or heterocyclic group, and $R^3$ represents a substituted or unsubstituted alkyl, alkenyl, or alkynyl group, or a reversibly attached protective group.

2. The process according to claim 1, further comprising:
b) isolating a compound of formula I from a reaction mixture.

3. The process according to claim 2, further comprising:
c) subjecting the compound of formula I obtained in b) to dehydrating conditions to obtain a compound of formula IV:

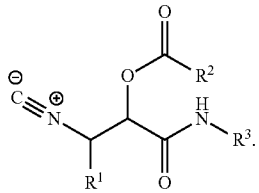
(IV)

4. The process according to claim 3, further comprising:
reacting the compound of formula IV with a compound of formula IX or a diastereomer thereof:

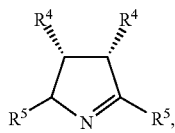
(IX)

and a compound of the general formula X:

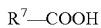
(X), to obtain a compound of formula XI or a diastereomer thereof:

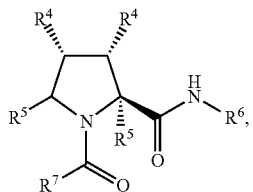
(XI)

wherein $R^4$ represents each independently, or jointly a substituted or unsubstituted alkyl, alkenyl, alkynyl, aromatic or non-aromatic, mono-, di- or tricyclic, or heterocyclic group, $R^5$ represents each independently a hydrogen atom, a substituted or unsubstituted alkyl, alkenyl, alkynyl, aromatic or non-aromatic, mono-, di- or tricyclic, or heterocyclic group, $R^6$ represents the structure derived from compound I, wherein the formyl carbon atom is linked to the proline ring, while the hydrogen atom has been removed and wherein $R^1$, $R^2$ and $R^3$ are defined herein above, and $R^7$ represents a substituted or unsubstituted alkyl, alkenyl, or alkynyl, or an aromatic or non-aromatic aromatic or non-aromatic, mono-, di- or tricyclic, or heterocyclic group.

5. The process according to claim 4, wherein both substituents $R^4$ jointly form a substituted or unsubstituted 3-, 4-, 5-, 6-, 7- or 8-membered ring structure.

6. The process according to claim 5, wherein $R^4$ is chosen such that the compound of formula I has a structure of formula XII, XIII or XIV:

(XII)

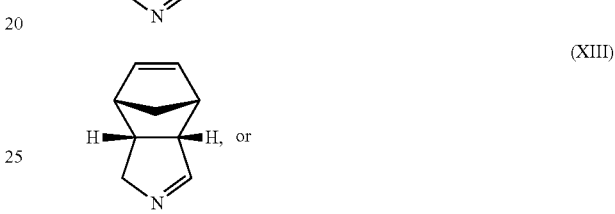
(XIII)

(XIV)

7. The process according to claim 4, wherein $R^7$ represents a structure of formula XV:

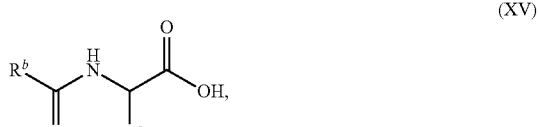
(XV)

wherein $R^a$ and $R^b$ each independently represents a hydrogen atom, a halogen atom, $C_1$-$C_4$ alkyl optionally substituted by halogen, a cycloalkyl group, an aryl group, a lower alkoxy group, a lower thioalkyl group, a cycloalkyloxy group, an aralkyloxy group or an alkanoyl group; a hydroxyl group, a nitro group, a formyl group, an amino group which may be protected or substituted, a cycloalkyloxy, aralkyloxy, alkanoyl, ureido or mono-, di- or tricyclic heterocyclic group, all of which groups may optionally be substituted.

8. The process according to claim 1, wherein $R^1$ is —$CH_2$-cyclopropyl or —$CH_2$-cyclobutyl.

9. The process according to claim 1, wherein $R^2$ is acetate.

10. The process according to claim 1, wherein R is cycloalkyl or hydrogen.

11. The process according to claim 1, wherein $R^1$, $R^2$ and $R^3$ are chosen such that the compound of formula VI has a structure of formula VII:

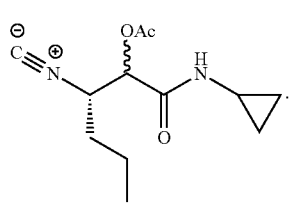
(VII)

12. The process according to claim 1, wherein the aldehyde of formula II has been derived from a substantially enantiomerically pure substituted-amino-1-ethanol of formula V:

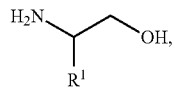
(V)

by A) N-formylation and B) subsequent Dess-Martin oxidation of the N-formylated intermediate.

13. The process according to claim 12, wherein the Dess-Martin oxidation is carried out in the presence of $R^3$—NC, so that the acetic acid liberated as a by-product of the Dess-Martin oxidation reacts as $R^2$—COOH.

14. The process according to claim 1, further comprising: formulating the compound of formula I to a pharmaceutical composition.

15. A compound obtained by the process of claim 1.

* * * * *